United States Patent [19]
Bhatt et al.

[11] Patent Number: 5,597,584
[45] Date of Patent: Jan. 28, 1997

[54] METHOD OF CONTROLLING RELEASE OF AN ACTIVE OR DRUG FROM A SILICONE RUBBER MATRIX

[75] Inventors: Padmanabh P. Bhatt; Victor A. Raul, both of Midland, Mich.

[73] Assignee: Dow Corning Corporation, Midland, Mich.

[21] Appl. No.: 510,249

[22] Filed: Aug. 2, 1995

Related U.S. Application Data

[63] Continuation of Ser. No. 261,790, Jun. 20, 1994, abandoned.
[51] Int. Cl.$^6$ ................................................ A61K 9/14
[52] U.S. Cl. ................................................ 424/486; 528/15
[58] Field of Search .............................. 424/486; 528/15

[56] References Cited

U.S. PATENT DOCUMENTS 4,814,184   3/1989   Aquadisch et al. ................ 424/445

OTHER PUBLICATIONS

Pfister, Fraleigh and Walters, "Characterization of a New Polydimethylsiloxane Elastomer Resistant to Drug Induced Cure Inhibition; Matrix for Controlled Drug Delivery"; Presented at the 17th International Symposium on Controlled Release of Bioactive Materials, Jul. 22–25 1990, Reno Nevada. Proceed. Intern. Symp. Control Rel. Bioact. Mater. 17:277–278 (1990).

*Primary Examiner*—Melvyn I. Marquis
*Attorney, Agent, or Firm*—Sharon K. Severance

[57] ABSTRACT

The instant invention pertains to a method of controlling release of active agents or drugs from a silicone rubber matrix by controlling the degree of crosslinking in the silicone rubber matrix. The silicone rubber matrixes of the instant invention are produced from liquid silicone rubbers comprised of (A) a polyorganosiloxane containing at least two alkenyl radicals per molecule; (B) an organohydrogensiloxane containing at least two silicon-bonded hydrogen atoms per molecule; and (C) a hydrosilylation catalyst in an amount sufficient to promote curing of said composition.

25 Claims, No Drawings

METHOD OF CONTROLLING RELEASE OF AN ACTIVE OR DRUG FROM A SILICONE RUBBER MATRIX

This is a continuation of application Ser. No. 08/261,790 filed on Jun. 20, 1994 and now abandoned.

BACKGROUND OF THE INVENTION

There are several methods known in the art for controlling the release from a silicone rubber matrix. One method is incorporate a water soluble additives such as polyethylene, ethylene glycol, glycerol, or lactose into the silicone rubber matrix. The water soluble additive affects the swelling of the silicone rubber matrix and thereby provides a means for controlling the release of the drug or active. JP 59044310 discloses a composition comprising a silicone rubber base, an active ingredient and a powdered dissolution assistant. The powdered dissolution assistants include monobasic alpha-amino acids (glycine and alanine), sodium chloride or mannitol. The compositions disclosed in JP 59044310 are useful for implantation or insertion into the body and can release the active ingredient over a period of one week to one month.

Carelli et al. have evaluated the effects of various agents on swelling of a silicone rubber matrix with or without varying amounts of specific drugs. In "Effect of Different Water-Soluble Additives on the Sustained Release of Sulfanilamide from Silicone Rubber Matrices" IL Farmaco Edizione Pratica, 37(12), pp. 377–389 (1982) Catelli et al. evaluated the effects of ethylene glycol, glycerol, polyethylene glycols, polysorbate 80, sodium chloride and sodium alginate to release sulfanilamide from a medical grade silicone rubber to an isotonic pH 7.4 phospate buffer at controlled rates. Additionally, in "Effect of Different Water-Soluble Additive on Water Sorption into Silicone Rubber" Journal of Pharmaceutical Sciences, Bol. 73, No. 3, pp. 316–317 (1983) Catelli et al. evaluated the ability of ethylene glycol, glycerin, polyethylene glycols, polysorbate 80 and lactose dispersed individually in silicone rubber to promote water sorption into the polymer.

Another method for controlling the release of a drug from a silicone rubber matrix is by controlling the amount, type and particle size of the drug loaded into the silicone rubber matrix. For example, in "Release of Osmotically Active Drugs from Silicone Rubber Matrixes", IL Farmaco Edizione Pratica, 39(9), pp. 310–319 (1984) Catelli et al. evaluated the release of osmotically active drugs (sodium salicylate and lidocaine hydrochloride) dispersed in a silicone rubber matrix from the water swollen matrix to isotonic pH 7.4 phosphate buffer. Carelli et al. theorize that the release is via a self-triggered osmotic pumping mechanism via cracks having formed in the stressed polymer.

It is an object of the instant invention to provide a method for controlling the release of active agents or drugs from a silicone rubber matrix by controlling the cross-link density of the silicone rubber matrix.

SUMMARY OF THE INVENTION

The instant invention pertains to a method of controlling release of active agents or drugs from a silicone rubber matrix by controlling the degree of crosslinking in the silicone rubber matrix. The silicone rubber matrixes Of the instant invention are produced by curing a liquid silicone rubber comprised of (A) a polyorganosiloxane containing at least two alkenyl radicals per molecule; (B) an organohydrogensiloxane containing at least two silicon-bonded hydrogen atoms per molecule; and (C) a hydrosilylation catalyst in an amount sufficient to promote curing of Said composition.

THE INVENTION

The instant invention pertains to a method of controlling release of an active agent or drug from a silicone rubber matrix by controlling the degree of crosslinking in the silicone rubber matrix. The degree of crosslinking of the cured rubber may be controlled by several factors including the location and concentration of the active sites on the polyorganosiloxane (A), the location and concentration of active sites on the organohydrogensiloxane (B), and the concentration of active sites on a filler-treating agent. The silicone rubber matrixes of the instant invention are produced by curing liquid silicone rubbers comprised of:

(A) a polyorganosiloxane containing at least two alkenyl radicals per molecule;

(B) an organohydrogensiloxane containing at least two silicon-bonded hydrogen atoms per molecule; and (C) a hydrosilylation catalyst in an amount sufficient to promote curing of said composition.

The liquid silicone rubber compositions of the instant invention are capable of curing at temperatures below 100° C. It should be noted that when the drug is combined with the liquid silicone rubbers of the instant invention that curing at temperatures above 100° C. may be necessary to effectively cure the liquid silicone rubber. One skilled in the art will be able to determine the temperature at which the rubber will effectively cure.

Polyorganosiloxane (A) of the liquid silicone rubber composition is the principal ingredient of these compositions. polyorganosiloxane (A) must contain at least two silicon-bonded alkenyl radicals in each molecule. Suitable alkenyl radicals contain from 1 to about 10 carbon atoms and are exemplified by but not limited to vinyl, allyl and 5-hexenyl. The remaining silicon-bonded radicals are selected from organic groups other than alkenyl radicals. The silicon-bonded organic groups are selected from monovalent hydrocarbon and halogenated hydrocarbon radicals exemplified by but not limited to alkyl radicals such as methyl, ethyl and propyl; aryl radicals such as phenyl; and halogenated alkyl radicals such as 3,3,3-trifluoropropyl.

The molecular structure of polyorganosiloxane (A) is typically linear, however there can be some branching due to the presence of trivalent siloxane units within the molecule. To achieve a useful level of tensile properties in the elastomers prepared by curing the present compositions, the molecular weight of this ingredient should be sufficient to achieve a viscosity at 25° C. greater than about 100 mPa.s. The upper limit for the molecular weight of polyorganosiloxane (A) is not specifically restricted, and is typically limited only by the processability of the curable organosiloxane composition. The polyorganosiloxanes range from pourable liquids to gum type polymers that are typically characterized by Williams plasticity values. Preferably polyorganosiloxane (A) should have a viscosity of 100 to 1,000,000 mPa.s, more preferably from 500 to 100,000 mPa.s.

Preferably polyorganosiloxane (A) is selected from polyorganosiloxanes of the formula

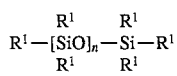

(I)

where each $R^1$ is individually selected from the group consisting of monovalent hydrocarbon radicals, monovalent halohydrocarbon radicals and an alkenyl radical with the proviso that at least two $R^1$ groups are alkenyl radicals; and n represents a degree of polymerization equivalent to a viscosity of at least 100 mPa.s It is further preferred that polyorganosiloxane (A) is a polyorganosiloxane represented by the general formula

  (II)

where each $R^2$ is individually selected from the group consisting of monovalent hydrocarbon radicals and monovalent halohydrocarbon radicals; $R^3$ represents an alkenyl radical; and n represents a degree of polymerization equivalent to a viscosity of at least 100 mPa.s, preferably from 100 to 1,000,000 mPa.s.

In the above formula for polyorganosiloxane (A) each $R^1$ is individually selected from the group consisting of monovalent hydrocarbon radicals, monovalent halohydrocarbon radicals and an alkenyl radical with the proviso that at least two $R^1$ groups are alkenyl radicals. Each $R^1$ can be identical or different, and can contain from 1 to about 20 carbon atoms, however at least two $R^1$ groups should be alkenyl groups. It is preferred that $R^1$ contains from 1 to 10 carbon atoms based on the availability of the corresponding monomers. Most preferably at least two $R^1$ groups are vinyl and any remainder are methyl, this preference being based on the availability of the reactants typically used to prepare the polyorganosiloxane and the properties of cured elastomers prepared from these polyorganosiloxanes.

Each $R^2$ is individually selected from the group consisting of monovalent hydrocarbon radicals and monovalent halohydrocarbon radicals. $R^2$ may be exemplified by methyl, ethyl, phenyl, 3,3,3-trifluoropropyl and others. Preferably $R^2$ is methyl. $R^3$ represents an alkenyl radical $R^3$ is preferably vinyl or 5-hexenyl.

Polyorganosiloxane (A) containing alkenyl radicals only at the terminal positions (formula II) may be exemplified by, but not limited to dimethylvinylsiloxy-terminated polydimethylsiloxanes, dimethylvinylsiloxy-terminated polymethyl-3,3,3-trifluoropropylsiloxanes, dimethylvinylsiloxy-terminated -dimethylsiloxane/3,3,3-trifluoropropylmethylsiloxane copolymers and dimethylvinylsiloxy-terminated-dimethylsiloxane/methylphenylsiloxane copolymers.

Methods for preparing polyorganosiloxane (A) of the instant invention are well known in the art. These methods include hydrolysis and condensation of the corresponding halosilanes or by condensation of the cyclic polyorganosiloxanes.

The liquid silicone rubber compositions of this invention contain at least one organohydrogensiloxane (B) that functions as a crosslinker for polyorganosiloxane (A). In the presence of the hydrosilylation catalyst (C) the silicon-bonded hydrogen atoms in the organohydrogensiloxane (B) undergo an addition reaction, referred to as hydrosilylation, with the silicon-bonded alkenyl groups in polyorganosiloxane (A), resulting in crosslinking and curing of the composition.

Organohydrogensiloxane (B) must contain at least 2 silicon-bonded hydrogen atoms in each molecule. If polyorganosiloxane (A) contains only two alkenyl radicals per molecule, organohydrogensitoxane (B) must contain an average of more than two silicon-bonded hydrogen atoms to achieve a crosslinked structure in the final cured product. The silicon-bonded organic groups present in organohydrogensiloxane (B) are selected from the same group of monovalent hydrocarbon and monovalent halohydrocarbon radicals of polyorganosiloxane (A) (eg. $R^1$), with the proviso that the silicon-bonded organic groups in organohydrogensiloxane (B) must be substantially free of ethylenic or acetylenic unsaturation. The molecular structure of organohydrogensiloxane (B) can be straight chain, branch-containing straight chain, cyclic, or network.

While the molecular weight of organohydrogensiloxane (B) is not specifically restricted, viscosities in the range of 3 to 10,000 mPa.s at 25° C. are preferred.

The concentration of organohydrogensiloxane (B) should be sufficient to provide a molar ratio of silicon-bonded hydrogen atoms to alkenyl radicals in the curable composition of from 0.5 to 20. A range of from 0.5 to 2 is preferred. When the curable composition contains less than 0.5 moles of silicon-bonded hydrogen atoms per mole of alkenyl radicals the composition cannot be satisfactorily cured. Bubble formation resulting from the generation of hydrogen gas can occur when the composition contains more than about 20 silicon-bonded hydrogen atoms per alkenyl radical.

Curing of the instant liquid silicone rubber compositions is achieved by catalyzing the composition with a hydrosilylation catalyst (C). Any hydrosilylation catalyst which affects the reaction between the organohydrogensiloxane (B) at an —Si—H and the polyorganosiloxane (A) at the —C=C— may be useful in the instant invention. Hydrosilylation catalysts useful in the instant invention may be exemplified by, but not limited to, rhodium compounds, platinum metal, platinum compounds, platinum complexes, nickel compounds, palladium metal and others. Platinum metal and platinum compounds are preferred based on the high activity level of these catalysts in hydrosilylation reactions.

The rhodium compounds useful in the instant invention may be exemplified by, but not limited to, rhodium metal, rhodium chloride and $RhCl_3(n-Bu_2S)_3$. The platinum catalysts useful in the instant invention may be selected from platinum metal on a support, platinum compounds and platinum complexes. The platinum compounds and platinum complexes may be exemplified by chloroplatinic acid, chloroplatinic acid hexahydrate, Karstedt's catalyst (Pt #2, Pt $(ViMe_2SiOSiViMe_2)_2$), dichloro-bis (triphenylphosphine) platinum (II), cis-dichloro-bis(acetonitrile)platinum(II), dicarbonyldichloroplatinum(II), platinum chloride, platinum oxide and others. The platinum metal can be deposited on a support such as charcoal, alumina, zirconia, among others. Any platinum containing material which effects the reaction between the silicon hydride and the unsaturated portion of the unsaturated compound is useful in the instant invention. A further description of platinum catalysts useful in the instant invention is found in, but not limited to, U.S. Pat. Nos. 4,578,497, 3,775,452, 3,220,972 and 2,823,218, herein incorporated by reference for what they teach about platinum catalysts per se.

The concentration of catalyst (C) in the present compositions is equivalent to a concentration of from 0.1 to 500 parts by weight of catalyst metal (eg. platinum metal), preferably from 1 to 50 parts by weight of catalyst metal, per million parts (ppm), based on the combined weight of components (A) and (B). Curing does not proceed satisfactorily at below 0.1 ppm of catalyst metal, while using more than 500 ppm results in no appreciable increase in cure rate, and is therefore uneconomical.

The catalyst may be dissolved in a solvent for ease of handling and to facilitate measuring the minute amounts needed. Preferably the solvent should be inert. Suitable solvents include silicone fluids such as polydimethylsiloxanes and dimethylvinylsiloxy-terminated polydimethylsiloxanes and hydrocarbon solvents such as benzene, toluene, xylene, and mineral spirits and polar solvents such as alcohols, various glycols and esters.

In addition to the aforementioned components (A), (B) and (C) additional components may be optionally added. Mixtures of the aforementioned components (A), (B) and (C) may begin to cure at ambient temperature. To delay or suppress the cure, the activity of the catalyst under ambient conditions can be retarded or suppressed by addition of a suitable inhibitor.

Known platinum catalyst inhibitors include, but are not limited to, the acetylenic compounds disclosed in U.S. Pat. No. 3,445,420, which issued on May 20, 1969 to Kookootsedes et Acetylenic alcohols such as 2-methyl-3-butyn-2-ol constitute a preferred class of inhibitors that will suppress the activity of a platinum-containing catalyst at 25° C. Compositions containing these catalysts typically require heating at temperatures of 70° C. or above to cure at a practical rate.

Inhibitor concentrations as low as one mole of inhibitor per mole of platinum will in some instances impart satisfactory storage stability and cure rate. In other instances inhibitor concentrations of up to 500 or more moles of inhibitor per mole of platinum are required. The optimum concentration for a given inhibitor in a given composition can readily be determined by routine experimentation and does not constitute part of this invention.

Some compositions may begin to cure under ambient conditions even when an inhibitor is present. One way to ensure storage stability is to package the ingredients of the curable composition in two or more containers, with the hydrosilylation catalyst and the organohydrogensiloxane in separate containers. The contents of the containers are combined when it is desired to cure the composition.

One-part organosiloxane compositions having excellent long-term storage stability at temperature of up to 50° C. or higher can be prepared by first microencapsulating the platinum-containing hydrosilylation catalyst in a thermoplastic or thermosetting polymer. Curable organosiloxane compositions containing microencapsulated hydrosilylation catalysts are described in U.S. Pat. Nos. 4,766,176, which issued on Aug. 23, 1988 and 5,017,654, which issued on May 21, 1991. The teaching of these patents relating to storage stable one-part organosiloxane compositions is incorporated herein by reference. Suitable encapsulants include but are not limited to organosilicon resins and organic resins derived from ethylenically unsaturated hydrocarbons and/or esters of ethylenically unsaturated carboxylic acids such as acrylic and methacrylic acids.

To achieve high levels of tear strength and other physical properties that characterize some types of cured elastomers that can be prepared using the compositions of this invention, it may be desirable to include a reinforcing filler such as finely divided silica. Silica and other reinforcing fillers are often treated with one of more of the known filler treating agents to prevent a phenomenon referred to as "creping" or "crepe hardening" during processing of the curable composition.

Finely divided forms of silica are preferred reinforcing fillers. Colloidal silicas are particularly preferred because of their relatively high surface area, which is typically at least 50 square meters per gram. Fillers having surface areas of at least 300 square meters per gram are preferred for use in the present method. Colloidal silicas can be of the precipitated or a fume type. Both types of silica are commercially available.

The amount of finely divided silica or other reinforcing filler used in the present compositions is at least in part determined by the physical properties desired in the cured elastomer. Liquid or pumpable rubber compositions typically contain from about 10 to about 60 percent by weight of silica, based on the weight of the rubber components (ie. polyorganosiloxane and organohydrogensiloxane). This value is preferably from about 30 to about 50 percent.

The filler treating agent can be any of the low molecular weight organosilicon compounds disclosed in the art as being, suitable for preventing creping of organosiloxane compositions during processing. The treating agents are typically liquid hydroxyl terminated polydiorganosiloxanes containing an average of from 2 to about 20 repeating units per molecule, and organosilicon compounds such as hexaorganodisiioxanes and hexaorganodisilazanes that hydrolyze under the conditions used to treat the filler to form compounds with silicon-bonded hydroxyl groups. Preferably at least a portion of the silicon bonded hydrocarbon radicals present on the treating agent are identical to a majority of the hydrocarbon radicals present in ingredients A and B. A small amount of water can be added together with the silica treating agent(s) as a processing aid.

It is believed that the treating agents function by reacting with silicon-bonded hydroxyl groups present on the surface of the silica or other filler particles to reduce interaction between these particles.

When a silica filler is used, it is preferably treated in the presence of at least a portion of the other ingredients of the present compositions by blending these ingredients together until the filler is completely treated and uniformly dispersed to form a homogeneous material.

The ingredients that are present during treatment of the filler typically include the silica treating agents and at least a portion of polyorganosiloxane (A).

The present organosiloxane compositions can further contain one or more additives that are conventionally present in curable compositions of this type to impart or enhance certain physical properties of the cured composition in addition to adhesion or to facilitate processing of the curable composition.

Typical additives include but are not limited to non-reinforcing fillers such as quartz, alumina, mica and calcium carbonate; pigments such as carbon black and titanium dioxide; dyes, flame retardants, and heat and/or ultraviolet light stabilizers. Resinous organosiloxane copolymers can be used in place of or in combination with one or more reinforcing fillers to improve the physical properties of the cured organosiloxane composition.

A preferred type of resinous copolymer contains repeating units of the general formula $SiO_{4/2}$ in addition to triorganosiloxy units of the general formulae $R^2_3SiO_{1/2}$ and diorganovinylsiloxy units of the general formula $$CH_2=CH(R^2)_2SiO_{1/2}$$

wherein $R^2$ is as defined above. The molar ratio of the combination of triorganosiloxy units and diorganovinylsiloxy units to $SiO_{4/2}$ units in the resinous copolymer is from 0.7 to 1.2, inclusive. The vinyl-containing units constitute from 2 to 8 percent by weight of the resinous copolymer, which preferably contains at least two vinyl radicals per molecule. It is preferred that the resinous copolymer have a molar ratio of diorganovinylsiloxy to triorganosiloxy:$SiO_{4/2}$ units of 0.08 to 0.1 : 0.06 to 1 : 1. The resinous copolymers can be prepared as described in U.S. Pat. No. 2,676,182, which issued to Daudt and Tyler on Apr. 20, 1954 and is hereby incorporated in this specification by reference thereto.

In addition to these components, other components which may effect the release of the drug or active from the silicone rubber matrix may be added. These release additives include, but are not limited to, ethylene glycol, glycerol, polyethylene glycols, polysorbate 80, sodium chloride and sodium alginate.

To maximize storage stability the curable compositions are preferably kept in closed containers until used. If greater storage stability is desired, the compositions can be packaged in two or more containers with the organohydrogensiloxane (B) and the hydrosilylation catalyst (C) in a separate container.

The silicone rubber matrixes of the instant invention can be prepared by combining all of ingredients at ambient temperature. Any of the mixing techniques and equipment described in the prior art can be used for this purpose. The particular equipment used will be determined by the viscosity of the ingredients and the final curable composition. Suitable mixers include but are not limited to paddle type mixers, kneader type mixers and two- and three-roll rubber mills. Cooling of the ingredients during mixing may be desirable to avoid premature curing of the composition.

Curing of the present compositions commences when components (A), (B) and (C) are combined. Preferred compositions cure over a period of several hours under ambient conditions. As is true for other compositions that cure by a platinum-catalyzed hydrosilylation reaction, curing can be accelerated by heating. The compositions of the instant invention can be cured at temperatures of less than 100° C., preferably at temperatures of from 25° C. to about 80° C.

Various crosslinking densities in the silicone rubber matrix can be achieved by varying several factors in the production of the silicone rubber matrix. These factors include increasing the SiH:C=C ratio to increase the cross link density; by employing reactants wherein the location of the SiH and/or C=C functionality is both terminal and pendant (as opposed to terminal only) to increase the crosslink density; and by employing a filler having active sites (i.e. SiOH) to increase the cross-link density, One skilled in the art will be able to determine the appropriate factors to produce the desired release rate of the particular drug being employed. It is theorized that by changing the cross-link density that the swelling characteristics of the silicone rubber matrix is changed resulting in changes or control of the release of the drug from the silicone rubber matrix.

Drugs that may be released from the silicone rubber matrix may be exemplified by, but not limited to, antibiotics such as tetracycline, chlortetracycline, bacitracin, neomycin, polymyxin, gramicidin, cephalexin, oxytetracycline, chloramphenicol, kanamycin, rifampicin, tobramycin, gentamicin, erythromycin and penicillin; antibacterials such as sulfonamides, sulfadiazine, sulfacetamide, sulfamethizole, and sulfisoxazole, nitrofurazone and sodium propionate; antivirals such as idoxuridine, trifluorothymidine, acyclovir, ganciclovir and interferon; antiallergenics such as sodium cromoglycate, antazoline, methapyriline, chlorpheniramine, cetirizine and prophenpyridadine; antiinflammatories such as hydrocortisone, hydrocortisone acetate, dexamethasone, dexamethasone 21-phosphate, fluocinolone, medrysone, prednisolone acetate, fluoromethalone, betamethasone, and triamcinolone; non-steroidal agents such as indomethacin, diclofenac, flurbiprofen, piroxicam, ibuprofen and acetyl salicylic acid; decongestants such as phenylephrine, naphazoline and tetrahydrozoline; miotics and anticholinesterase such as pilocarpine, acetylcholine chloride, physostigmine, eserine, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; immunological drugs such as vaccines and immune stimulants; hormonal agents such as estrogens, estradiol, progestational, progesterone, insulin, calcitonin, parathyroid hormone and peptide, vasopressin, hypothalamus releasing factor; beta adrenergic blockers such as timolol maleate, levobunolol HCl and betaxolol HCl; growth factors such as epidermal growth factor and fibronectin; carbonic anhydrase inhibitors such as dichlorphenamide, acetazolamide and methazolamide and other drugs such as prostaglandins, antiprostaglandins, and prostaglandin precursors.

The drugs may be used in conjunction with a pharmaceutically acceptable carrier. Examples of pharmaceutically acceptable carriers include solids such as starch, gelatin, sugars, e.g. glucose, natural gums, e.g. acacia; sodium alginate, carboxymethyl cellulose, polymers, e.g. silicone, liquids such as sterile water, saline, dextrose, dextrose in water or saline; condensation products of castor oil and ethylene oxide liquid glyceryl triester of a lower molecular weight fatty acid; lower alkanols; oils such as corn oil, peanut oil, sesame oil, and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxy-methylcellulose, sodium alginate, poly(vinylpyrolidone), alone, or with suitable dispensing agents such a lecithin, polyoxyethylene stearate. The carrier may also contain adjuvants such as preserving, stabilizing, wetting or emulsifying agents.

It is preferred that the drug to be released from the silicone rubber matrix is soluble in an aqueous medium or is modified to produce a soluble form thereof, for example a salt of a non or slightly soluble drug. A drug which is not soluble in an aqueous medium will not effectively release from the silicone rubber matrix. In addition to modifying the drug to produce a soluble form, release additives, discussed above, can be added to the liquid silicone rubber or silicone rubber matrix to allow for the release of drugs which are not readily soluble or slightly soluble in an aqueous medium.

The drug is loaded into the silicone rubber by matrix blending or mixing with the liquid silicone rubber at levels up to 40 weight percent of the total weight along with any other necessary excipients or release modifiers. The drug is solidified into the silicone rubber matrix by curing the liquid silicone rubber while being molded into the desired shape.

The drug may also be loaded into the silicone rubber matrix by solution impregnation in situations where the drug may hinder or prevent the curing of the liquid silicone rubber. This procedure consists of soaking the silicone rubber matrix in a solvent solution of the drug wherein the solvent is capable of causing the silicone rubber matrix to swell thereby allowing the drug to diffuse into the silicone rubber matrix. The silicone rubber matrix is then removed from the solvent and dried to produce the drug-impregnated system. One skilled in the art will be able to readily select a solvent that is compatible with the drug and allow the silicone rubber matrix to swell. Suitable solvents include, but are not limited to, xylene, heptane, methanol and chloroform.

The mechanism for release of the drug from the silicone rubber matrix is for example diffusion or osmosis. The period for release of the drug from the silicone rubber matrix can vary, for example, from hours up to 14 days or longer. So that those skilled in the art can understand and appreciate the invention taught herein, the following examples are presented, it being understood that these examples should not be used to limit the scope of this invention found in the claims attached hereto. Unless otherwise stated all viscosities are at 25° C.

Modulus (G') of the silicone rubber matrixes were determined using a Rheometrics Dynamic Spectrometer, Model DMTA, available from Rheometrics, Piscataway N.J., on 7 mmx1.88 mmx0.019 mm slabs at a frequency of 1 Hz at 40° C. From the modulus the cross-link density of the silicone rubber matrix could be calculated by calculating the molecular weight between cross-links ($M_c$). A smaller $M_c$ indicates a higher degree of cross-linking in the rubber.

The following silicone rubber matrixes were used:

RUBBER 1: A liquid silicone rubber was prepared by combining 1 part of a mixture containing approximately 65 wt % of a dimethylvinylsiloxy-terminated dimethylsiloxane having a plasticity of approximately 60 mils, 5 wt % of a dimethylvinylsiloxane-terminated methylvinyl dimethylsiloxane having a plasticity of approximately 60 mils, 0.7 wt % of a hydroxy-terminated methylvinyl dimethylsiloxane having a viscosity of approx. 40 mPa.s, 7 wt % of a hydroxy-terminated dimethylsiloxane having a viscosity of approx. 40 mPa.s, 21 wt % of amorphous silica and 0.35 wt % of a chloroplatinic acid complex of divinyltetramethyldisiloxane diluted with dimethylvinylsiloxy-terminated polydimethylsiloxane to provide 0.65 weight percent platinum with 1 part of a mixture containing approximately 64 wt % of a dimethylvinylsiloxy-terminated dimethylsiloxane having a plasticity of approximately 60 mils, 5 wt % of a dimethylvinylsiloxane-terminated methylvinyl dimethylsiloxane having a plasticity of approximately 60 mils, 0.7 wt % of a hydroxy-terminated methylvinyl dimethylsiloxane having a viscosity of approx. 40 mPa.s, 7 wt % of a hydroxy-terminated dimethylsiloxane having a viscosity of approx. 40 mPa.s, 21 wt % of amorphous silica and 2 wt % of a trimethylsiloxy-terminated methylhydrogen dimethylsiloxane having an average silicon-bonded hydrogen atom content of approximately 0.75 wt % and a viscosity of approximately 5 $mm^2$/s. The resulting composition had an SiH:C=C ratio of 4.7. A silicone rubber matrix was produced by curing the liquid silicone rubber at 115° C. for 10 minutes. The silicone rubber matrix had a modulus of 5.85 Pa which correlates to a $M_c$ of 4045 c/mole.

RUBBER 2: A liquid silicone rubber was prepared by combining 1 part of a mixture containing approximately 50 wt % of a dimethylvinylsiloxy-terminated dimethylsiloxane having a plasticity of approximately 60 mils, 6 wt % of a dimethylvinylsiloxane-terminated methylvinyl dimethylsiloxane having a plasticity of approximately 60 mils, 0.3 wt % of a hydroxy-terminated methylvinyl dimethylsiloxane having a viscosity of approx. 40 mPa.s, 8 wt % of a hydroxy-terminated dimethylsiloxane having a viscosity of approx. 40 mPa.s, 34 wt % of amorphous silica and 0.35 wt % of a chloroplatinic acid complex of diethenyltetramethyldisiloxane diluted with dimethylvinylsiloxy-terminated dimethylsiloxane to provide approximately 0.63 weight percent platinum with 1 part of a mixture containing approximately 49 wt % of a dimethylvinylsiloxy-terminated dimethylsiloxane having a plasticity of approximately 60 mils, 6 wt % of a dimethylvinylsiloxane-terminated methylvinyl dimethylsiloxane having a plasticity of approximately 60 mils, 0.3 wt % of a hydroxy-terminated methylvinyl dimethylsiloxane having a viscosity of approx. 40 mPa.s, 8 wt % of a hydroxy-terminated dimethylsiloxane having a viscosity of approx. 40 mPa.s, 33 wt % of amorphous silica and 2 wt % of a trimethylsiloxy-terminated methylhydrogen dimethylsiloxane having an average silicon-bonded hydrogen atom content of approximately 0.75 wt % and a viscosity of approximately 5 $mm^2$/s. The resulting composition had an SiH:C=C ratio of 2.5. A silicone rubber matrix was produced by curing the liquid silicone rubber at 115° C. for 10 minutes. The silicone rubber matrix had a modulus of 6.38 Pa which correlates to a $M_c$ of 1652 g/mole.

Rubber 3: A liquid silicone rubber was prepared by combining 10 parts of a mixture comprising 68 wt % of a dimethylvinylsiloxy-terminated dimethylsiloxane having a viscosity of 2100 mPa.s, 0.09 wt % of a chloroplatinic acid complex of divinyltetramethyldisiloxane diluted with dimethylvinylsiloxy-terminated polydimethylsiloxane to provide 0.65 weight percent platinum and 31 wt % of hexamethydisilazan treated silica with 1 part of a mixture containing 87.7 wt % of the same dimethylvinylsiloxy-terminated dimethylsiloxane, 12 wt % of a trimethylsiloxy-terminated methylhydrogen dimethylsiloxane having an average silicon-bonded hydrogen atom content of approximately 0.75 weight percent and a viscosity of approximately 5 $mm^2$/s and 0.3 wt % of tetramethyltetravinylcyclotetrasiloxane. The resulting composition had an SiH:C=C ratio of 1.4. A silicone rubber matrix was produced by curing the liquid silicone rubber at 150° C. for 3 minutes. The silicone rubber matrix had a modulus of 5.60 Pa which correlates to a $M_c$ of 7233 g/mole.

RUBBER 4: A liquid silicone rubber was prepared by combining 1 part of a mixture containing approximately 68 wt % of a dimethylvinylsiloxy-terminated dimethylsiloxane having a viscosity of 35,000 mPa.s, 0.7 wt % of a hydroxy-terminated methylvinyl dimethylsiloxane having a viscosity of approx. 40 mPa.s, 0.8 wt % of a hydroxy-terminated dimethylsiloxane having a viscosity of approx. 40 mPa.s, 0.18 wt % of a chloroplatinic acid complex of divinyltetramethyldisiloxane diluted with dimethylvinylsiloxy-terminated polydimethylsiloxane to provide 0.65 weight percent platinum and 29 wt % of hexamethydisilazane treated silica with 1 part of a mixture containing approximately 65 wt % of a dimethylvinylsiloxy-terminated dimethylsiloxane having a viscosity of 35,000 mPa.s, 0.7 wt % of a hydroxy-terminated methylvinyl dimethylsiloxane having a viscosity of approx. 40 mPa.s, 0.8 wt % of a hydroxy-terminated dimethylsiloxane having a viscosity of approx. 40 mPa.s, 29 wt % of hexamethyldisilazane treated silica and 3 wt % of a trimethylsiloxy-terminated methylhydrogen dimethylsiloxane having an average silicon-bonded hydrogen atom content of approximately 0.75 weight percent and a viscosity of approximately 5 $mm^{2/}$s. The resulting composition had an SiH:C=C ratio of 1.4. A silicone rubber matrix was produced by curing the liquid silicone rubber at 150° C. for 5 minutes.

RUBBER 5: A liquid silicone rubber was prepared by combining 1 part of a mixture containing approximately 51 wt % of a dimethylvinylsiloxy-terminated dimethylsiloxane having a viscosity of 55,000 mPa.s, 7 wt % of a dimethylvinylsiloxy-terminated methylvinyl dimethylsiloxane having a viscosity of 350 mPa.s, 0.6 wt % of a hydroxy-terminated methylvinyl dimethylsiloxane having a viscosity of approx. 40 mPa.s, 0.1 wt % of a hydroxy-terminated dimethylsiloxane having a viscosity of approx. 40 mPa.s, 0.18 wt % of a chloroplatinic acid complex of divinyltetramethyldisiloxane diluted with dimethylvinylsiloxy-terminated polydimethylsiloxane to provide 0.65 weight percent platinum and 40 wt % of hexamethydisilazane treated silica with 1 part of a mixture containing approximately 49 wt % of a dimethylvinylsiloxy-terminated dimethylsiloxane having a viscosity of 55,000 mPa.s, 7 wt % of a dimethylvinylsiloxy-terminated methylvinyl dimethylsiloxane having a viscosity of 350 mPa.s, 0.5 wt % of a hydroxy-terminated methylvinyl dimethylsiloxane having a viscosity of approx. 40 mPa.s, 0.1 wt % of a hydroxy-terminated dimethylsiloxane having a viscosity of approx. 40 mPa.s, 39 wt % of hexamethydisilazane treated silica and 3 wt % of a trimethylsiloxy-terminated methylhydrogen dimethylsiloxane having an average Silicon-bonded hydrogen atom content of approximately 0.75 weight percent and a viscosity of approximately 5 mm$^2$/s. The resulting composition had an SiH:C=C ratio of 1.7. A silicone rubber matrix was produced by curing the liquid silicone rubber at 150° C. for 5 minutes. The silicone rubber matrix had a modulus of 6.11 Pa which correlates to a $M_c$ of 2324.

EXAMPLE 1

203.2 mm×203.2 mm×0.018 mm slabs of silicone rubber matrixes were produced by curing the rubbers listed in Table 1 according to the cure conditions given above. Circular discs, each weighing approximately 0.75 grams were cut out the silicone matrixes and weighed. After they were weighed the discs were individually placed in a closed containers containing . approximately 25 grams of heptane. After 3, 4, 6 and 9 days the discs were removed and patted dry and weighed. The results in Table 1 show the various weight gains in percent.

TABLE 1

| Rubber | 3 Days | 4 Days | 6 Days | 9 Days |
|---|---|---|---|---|
| Rubber 1 | 216.0 | 219.1 | 221.2 | 221.2 |
| Rubber 2 | 127.6 | 128.4 | 129.7 | 130.5 |
| Rubber 3 | 218.8 | 219.3 | 219.3 | 219.8 |
| Rubber 4 | 149.8 | 150.2 | 151.1 | 150.7 |
| Rubber 5 | 111.1 | 112.0 | 112.8 | 112.0 |

EXAMPLE 2

Cylindrical rods were prepared by blending either Rubbers 1, 3, or 5 with the amount (wt %) of Oxytetracycline HCl shown in Table 2. The oxytetracycline/liquid silicone rubber mixture was placed under vacuum of about 28 inches of mercury for 30 minutes. Rubber 1 was forced into a cylinder situated in a transfer press and forced at 1500 psi for 3 minutes into a 12 cavity aluminum mold heated to 115° C. Rubber 3 was forced into a cylinder situated in a transfer press and forced at 1400 psi for 3 minutes into a 12 cavity aluminum mold to 115° C. Rubber 5 was forced into a cylinder situated in a transfer press and forced at 900 psi for 5 minutes into a 12 cavity aluminum mold to 115° C. The molds were kept under 10 tons of clamp pressure. The molds were then cooled, separated and the formed rods were removed.

The rods were then placed in Ghannan-Chien cells in 200 ml of a medium of either distilled water (Rubbers 1 and 3) or pH 7.4 phosphate buffer (Rubber 5). Samples of the medium were withdrawn at the times shown in Table 2 and analyzed by spectrophotometric assay at 276 nm (distilled water) and 272 nm (phosphate buffer) to determine the amount of drug in the medium. The results are reported in Table 2. Additionally the rods were removed from the medium, patted dry and weighed at the specified times to determine the swelling of the rods. The results in Table 2 show the various weight gains of the rods.

TABLE 2

| Wt % Oxytetracycline HCl | | 10 | 10 | 15 | 15 | 20 | 20 | 30 | 30 |
|---|---|---|---|---|---|---|---|---|---|
| Silicone Rubber Matrix | | 1 | 5 | 3 | 5 | 3 | 5 | 3 | 5 |
| Drug Release (μg/rod) | Day | | | | | | | | |
| | 1 | 118.2 | 115.1 | 238.7 | 238.8 | 339.6 | 384.7 | 812 | 1508.9 |
| | 4 | | 160.8 | 254.8 | 356.8 | 334.7 | 664.5 | 1273.3 | 4031.2 |
| | 7 | | 266.6 | 254.8 | 481.7 | 389.0 | 990.0 | 1615.9 | 5931.4 |
| | 10 | | 258.6 | 254.8 | 560.1 | 419.0 | 1322.8 | 1877.2 | 7449.4 |
| | 14 | | 300.6 | 260.0 | 664.7 | 501.8 | 1993.0 | 2393.3 | 9274.7 |
| Weight (mg) | Day | | | | | | | | |
| | 0 | | 46.3 | | 46.8 | 51 | 47.2 | | 51.8 | 48.9 |
| | 4 | | 53.0 | | 57.1 | | 65.4 | | | 84.6 |
| | 7 | | 56.3 | | 62.0 | 160 | 74.3 | | | 89.4 |
| | 10 | | 58.2 | | 66.7 | | 81.2 | | | 82.2 |
| | 14 | | 61.3 | | 71.9 | 186 | 87.2 | | 296 | 73.8 |

What is claimed is:

1. A method of controlling release of a drug from a silicone rubber matrix having a crosslink density comprising
   (A) loading a drug into a liquid silicone rubber comprising
      (a) a polydiorganosiloxane containing at least two alkenyl radicals per molecule;
      (b) a organohydrogensiloxane containing at least two silicon-bonded hydrogen atoms per molecule; and
      (c) a hydrosilylating catalyst in an amount sufficient to promote curing of the liquid silicone rubber;
   wherein the organohydrogensiloxane (b) is present in an amount sufficient to provide a molar ratio of alkenyl radicals in polyorganosiloxane (a) to silicon-bonded hydrogen atoms in organohydrogensiloxane (b) of from 0.5:1 to 20:1;
   (B) curing the liquid silicone rubber while being molded into a shape;
   (C) thereafter releasing the drug at a rate;
   wherein the rate of release is controlled by changing the crosslink density of the silicone rubber matrix.

2. A method as claimed in claim 1 wherein the polyorganosiloxane (A) is selected from polyorganosiloxanes having the formula

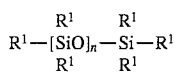

where each $R^1$ is individually selected from the group consisting of monovalent hydrocarbon radicals, monovalent halohydrocarbon radicals and an alkenyl radical with the proviso that at least two $R^1$ groups are alkenyl radicals; and n represents a degree of polymerization equivalent to a viscosity of at least 100 mPa.s.

3. A method as claimed in claim 1 wherein the polyorganosiloxane is selected from polyorganosiloxanes having the formula

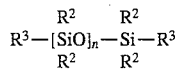

where each $R^2$ is individually selected from the group consisting of monovalent hydrocarbon radicals and monovalent halohydrocarbon radicals; $R^3$ represents an alkenyl radical; and n represents a degree of polymerization equivalent to a viscosity of at least 100 mPa.s.

4. A method as claimed in claim 1 wherein polyorganosiloxane (A) is a dimethylvinylsiloxy-terminated polydimethylsiloxane.

5. A method as claimed in claim 1 wherein polyorganosiloxane (A) is a mixture of a dimethylvinylsiloxy-terminated polydimethylsiloxane and a dimethylvinylsiloxane-terminated methylvinyl dimethylpolysiloxane.

6. A method as claimed in claim 1 wherein polyorganosiloxane (A) has a viscosity of 100 to 1,000,000 mPa.s at 25° C.

7. A method as claimed in claim 1 wherein organohydrogensiloxane (B) has a viscosity of 3 to 10,000 mPa.s at 25° C.

8. A method as claimed in claim 1 wherein hydrosilylation catalyst (C) is a platinum metal deposited on a support.

9. A method as claimed in claim 1 wherein the hydrosilylation catalyst (C) is a platinum compound.

10. A method as claimed in claim 1 wherein the hydrosilylation catalyst (C) is a platinum complex.

11. A method as claimed in claim 1 wherein the liquid silicone rubber further comprises a filler.

12. A method as claimed in claim 1 wherein the liquid silicone rubber further comprises a catalyst inhibitor.

13. A method as claimed in claim 1 wherein the liquid silicone rubber further comprises a release additive.

14. A method as claimed in claim 13 wherein the release additive is selected from the group consisting of ethylene glycol, glycerol, polyethylene glycols, polysorbate 80, sodium chloride and sodium alginate.

15. A method as claimed in claim 1 wherein the drug is soluble in an aqueous medium.

16. A method of controlling release of a drug from a silicone rubber matrix having a crosslink density comprising (A) curing a liquid silicone rubber while being molded into a shape wherein said liquid silicone rubber comprises (a) a polydiorganosiloxane containing at least two alkenyl radicals per molecule;

(b) a organohydrogensiloxane containing at least two silicon-bonded hydrogen atoms per molecule; and (c) a hydrosilylating catalyst in an amount sufficient to promote curing of the liquid silicone rubber;

wherein the organohydrogensiloxane (b) is present in an amount sufficient to provide a molar ratio of alkenyl radicals in polyorganosiloxane (a) to silicon-bonded hydrogen atoms in organohydrogensiloxane (b) of from 0.5:1 to 20:1;

(B) loading a drug into the cured liquid silicone rubber;

(C) thereafter releasing the drug at a rate from the matrix;

wherein the rate of release is controlled by changing the crosslink density of the silicone rubber matrix.

17. A method as claimed in claim 16 wherein the polyorganosiloxane (a) is selected from polyorganosiloxanes having the formula

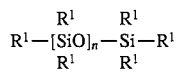

where each $R^1$ is individually selected from the group consisting of monovalent hydrocarbon radicals, monovalent halohydrocarbon radicals and an alkenyl radical with the proviso that at least two $R^1$ groups are alkenyl radicals; and n represents a degree of polymerization equivalent to a viscosity of at least 100 mPa.s.

18. A method as claimed in claim 16 wherein polyorganosiloxane (A) is a dimethylvinylsiloxy-terminated polydimethylsiloxane.

19. A method as claimed in claim 16 wherein polyorganosiloxane (a) is a mixture of a dimethylvinylsiloxy-terminated polydimethylsiloxane and a dimethylvinylsiloxane-terminated methylvinyl dimethylpolysiloxane.

20. A method as claimed in claim 16 wherein hydrosilylation catalyst (c) is selected from the group consisting of a platinum metal deposited on a support, a platinum compound, and a platinum complex.

21. A method as claimed in claim 16 wherein the liquid silicone rubber further comprises a filler.

22. A method as claimed in claim 16 wherein the liquid silicone rubber further comprises a catalyst inhibitor.

23. A method as claimed in claim 14 wherein the liquid silicone rubber further comprises a release additive.

24. A method as claimed in claim 23 wherein the release additive is selected from the group consisting of ethylene glycol, glycerol, polyethylene glycols, polysorbate 80, sodium chloride and sodium alginate.

25. A method as claimed in claim 16 wherein the drug is soluble in an aqueous medium.

* * * * *